United States Patent [19]

Henry et al.

[11] 4,291,157

[45] Sep. 22, 1981

[54] OCTANOYLHYDRAZONE DERIVATIVES OF ADRIAMYCIN

[75] Inventors: David W. Henry, Chapel Hill, N.C.; George L. Tong, Cupertino, Calif.

[73] Assignee: SRI International, Menlo Park, Calif.

[21] Appl. No.: 171,083

[22] Filed: Jul. 22, 1980

[51] Int. Cl.$^3$ .................. A61K 31/71; C07H 15/24
[52] U.S. Cl. ................................. 536/17 A; 424/180
[58] Field of Search ..................................... 536/17 A

[56] References Cited

U.S. PATENT DOCUMENTS

| 3,965,088 | 6/1976 | Jolles | 536/17 A |
| 4,112,217 | 9/1978 | Henry et al. | 536/17 A |
| 4,125,704 | 11/1978 | Henry et al. | 536/17 A |

Primary Examiner—Johnnie R. Brown
Attorney, Agent, or Firm—Donovan J. De Witt

[57] ABSTRACT

Adriamycin octanoylhydrazone, and its pharmaceutically acceptable salts, having good antitumor activity coupled with low toxicity.

2 Claims, No Drawings

OCTANOYLHYDRAZONE DERIVATIVES OF ADRIAMYCIN

BACKGROUND OF INVENTION

The Government has rights in this invention pursuant to Contract No. N01-CM-33742.

SUMMARY OF INVENTION

The present invention relates to the compound adriamycin octanoylhydrazone and to its pharmaceutically acceptable salts. Said compound, labeled NSC 233853 by the National Cancer Institute, has the structure

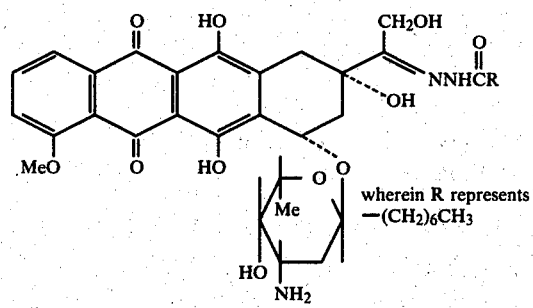

wherein R represents —$(CH_2)_6CH_3$

The compound presented above in structural form is preferably employed in the form of an acid addition salt with the free —$NH_2$ group present in the compound, since in such form the compound has enhanced solubility in water. However, it may be employed in non-salt form if so desired.

PRIOR ART

The prior art teaches derivatives of daunorubicin where R represents —$CH_3$, —$C_2H_5$, —$CH(CH_3)_2$ and —n—$C_{15}H_{31}$ (G. Jolles, R. Maral, M. Messer and G. Ponsinet, Antitumor Activity of Daunorubicin Derivatives, pp 237–241), (Chemotherapy, Vol. 8, Cancer Chemotherapy II, Plenum Press, New York and London (1975)). Table III, p 240 of the above reference, shows other derivatives where R is non-alkyl in character.

PARTICULARS OF INVENTION

Preparation of the HCl salt adriamycin octanoylhydrazone forms the subject of the following example. Biological test data showing the good antitumor characteristics of said product and its low cardiotoxicity are presented below.

EXAMPLE

Adriamycin Octanoylhydrazone Hydrochloride (I)

A solution of 1.16 g (2.0 mmole) of adriamycin hydrochloride and 1.58 g (10 mmole) of octanoylhydrazide in 325 ml of methanol was stirred at room temperature in the dark for 6 days. The reaction mixture was concentrated to about 100 ml and then allowed to stand at room temperature for 2 additional days. The reaction mixture was evaporated and the residue was triturated with 20 ml of methanol at room temperature in the dark overnight. The precipitate was collected, washed with 5×1 ml of methanol and dried at room temperature/0.1 mm/16 hr to afford the hydrazone (I) as an orange powder, 0.934 g (65%) mp 219°–221° decomposed. The mother liquors were evaporated and the residue was triturated with 20 ml of absolute ethanol to give an additional 0.188 g [total 1.122 g (78%)] of (I), mp 218°–220° decomposed.

| Anal. calc. for $C_{35}H_{45}N_3O_{11}$ . HCl . ½ $H_2O$ | | | |
|---|---|---|---|
| C | H | $Cl^\ominus$ | N |
| 57.65 | 6.50 | 4.86 | 5.76 |
| Found 57.58 | 6.49 | 4.80 | 5.82 |

It will be noted that the compound of this invention is prepared in the form of an acid addition salt with the free —$NH_2$ group of the compound.

These acid addition salts (shown herewith as that of HCl) are preferably the pharmaceutically acceptable, nontoxic addition salts with suitable acids, such as those with inorganic acids, for example, hydrochloric, hydrobromic, nitric, sulphuric and phosphoric acids, and with organic acids, such as organic carboxylic acids, for example, glycolic, maleic, hydroxymaleic, malic, tartaric, citric, salicylic acids, and organic sulphonic acids, for example, methanesulphonic and toluene-p-sulphonic acids.

An acid addition salt can be converted into the free compound according to known methods, for example, by treating it with a base, such as an alkali metal or alkaline earth metal hydroxide, for example, lithium hydroxide, sodium hydroxide, potassium hydroxide or calcuim hydroxide; with a metal carbonate, such as an alkali metal or an alkaline earth metal carbonate or hydrogen carbonate, for example sodium, potassium or calcium carbonate or hydrogen carbonate; with ammonia; or with a hydroxyl ion exchange resin, or with any other suitable reagent.

An acid addition salt may also be converted into another acid addition salt according to known methods; for example, a salt with an inorganic acid may be treated with a metal salt, for example, a sodium, barium and silver salt, of an acid in a suitable diluent, in which a resulting inorganic salt is insoluble and is thus removed from the reaction medium. An acid addition salt may also be converted into another acid addition salt by treatment with an anion exchange preparation.

The compound of this invention can be formulated as novel pharmaceutical preparations together with conventional pharmaceutical organic or inorganic carrier materials suitable for internal administration. Such preparations can be administered parenterally or orally, the dosages to be adjusted according to individual requirements. The novel pharmaceutical compositions can contain such conventional organic or inorganic inert carrier materials as water, gelatin, lactose, starch, magnesium stearate, talc, vegetable oils, gums, polyalkylene glycols, vaseline or the like. The pharmaceutical preparations can be in the conventional solid forms such as tablets, dragees, suppositories, capsules or in conventional liquid form such as solutions, suspensions of emulsions.

The pharmaceutical compositions can be submitted to conventional pharmaceutical expedients such as sterilization and/or can contain conventional pharmaceutical additives such as preservatives, stabilizing agents, wetting agents, emulsifying agents, salts for adjusting the osmotic pressure, buffers or the like. They also can contain other therapeutically useful materials.

BIOLOGICAL TESTS

Biological testing data for the compound of the present invention (as the HCl salt), as well as for adriamycin (for comparative purposes), are presented in the following table. Said data were obtained by testing said compounds against lymphocytic leukemia P388 implanted in mice, all under the auspices of the NCI and according to protocols which use the increased survival time of treated animals, compared to controls, as the measure of antitumor efficacy. Also included in the table are results obtained in the cardiotoxic evaluation of the indicated compounds in a reproducible screening system employing the rat, the data so obtained being referred to as the minimum cumulative cardiotoxic dose (MCCD). In these tests the rat model employs as end point the characteristic electrocardiographic changes that follow repreated administration of cardiotoxic anthracycline derivatives.

| Compound | NSC[a] No. | Minimum[b] Cumulative Cardiotoxic Dose in Rats mg/kg | Activity vs Leukemia P388 in Mice[c] | | | |
|---|---|---|---|---|---|---|
| | | | qd 1-9 Survival Time % T/C | Optimum Dose mg/kg | q4d 5,9,13 Survival Time % T/C | Optimum Dose mg/kg |
| | 233853 | 40 | 222 (1 test) | 3.12 | 179 (1 test) | 80 |
| Adriamycin | 123127 | 11 | 197 (8 tests) | 0.78 | 171 (106 tests) | 8 |

[a]Accession number of the National Cancer Institute.
[b]Assay described in G. Zbinden and E. Brandle, Cancer Chemo. Rpts., Part 1, 59, 707 (1975)
[c]Ip P388 murine leukemia treated ip on QD1-9 and Q4D 5, 9, 13 schedules according to standard NCI protocols. Assay described in R. I. Geran, N. H. Greenberg, M. M. MacDonald, A. M. Schumacher and B. J. Abbott, Cancer Chemother. Rep., Part 3, 3 (No. 2) 9 (1972), Protocol 1,200. T/C = ratio of survival time of treated mice to that of untreated controls times 100. Untreated controls survive about 9 days.

In addition to activity in the primary screen using P388 leukemia in mice, NSC 233853 shows activity in other mouse tumors: L1210 leukemia, B16 melanoma, CD8F, mammary tumor, and colon 38 tumor.

We claim:
1. Adriamycin octanoylhydrazone and its pharmaceutically acceptable acid addition salts.
2. The compound of claim 1 which is adriamycin octanoylhydrazone hydrochloride.

* * * * *